(12) United States Patent
Wilke

(10) Patent No.: US 8,961,758 B2
(45) Date of Patent: Feb. 24, 2015

(54) ION-SELECTIVE ELECTRODE

(75) Inventor: Stefan Wilke, Halle (DE)

(73) Assignee: Endress + Hauser Conducta Gesellschaft für Mess—und Regeltechnik mbH + Co. KG, Gerlingen (DE)

( * ) Notice: Subject to any disclaimer, the term of this patent is extended or adjusted under 35 U.S.C. 154(b) by 750 days.

(21) Appl. No.: 13/141,367

(22) PCT Filed: Nov. 27, 2009

(86) PCT No.: PCT/EP2009/065962
§ 371 (c)(1),
(2), (4) Date: Sep. 13, 2011

(87) PCT Pub. No.: WO2010/072510
PCT Pub. Date: Jul. 1, 2010

(65) Prior Publication Data
US 2011/0308946 A1 Dec. 22, 2011

(30) Foreign Application Priority Data

Dec. 22, 2008 (DE) .......................... 10 2008 055 084

(51) Int. Cl.
*G01N 27/333* (2006.01)
*G01N 27/403* (2006.01)
*G01N 27/28* (2006.01)

(52) U.S. Cl.
CPC .............. *G01N 27/28* (2013.01); *G01N 27/333* (2013.01)
USPC .......................... 204/416; 204/409; 204/412

(58) Field of Classification Search
CPC ............... G01N 27/333–27/401; G01N 27/36; G01N 27/403; G01N 35/085
See application file for complete search history.

(56) References Cited

U.S. PATENT DOCUMENTS

| 3,431,182 | A | | 3/1969 | Frant |
| 3,442,782 | A | * | 5/1969 | Shiller et al. .................. 204/419 |
| 3,647,666 | A | | 3/1972 | Simon |
| 3,835,011 | A | | 9/1974 | Baum |
| 4,889,611 | A | * | 12/1989 | Blough, Jr. .................... 204/411 |
| 5,417,836 | A | | 5/1995 | Masuda |

FOREIGN PATENT DOCUMENTS

DE 2021318 1/1971
(Continued)

OTHER PUBLICATIONS

M. Knoll et al., "Potentiometric silicon microsensor for nitrate and ammonium", Sensors and Actuators, B, Elsevier Sequoia S.A., Lausanne, Switzerland, Bd. 818, Nr. 1/03, 1994.
(Continued)

*Primary Examiner* — Alex Noguerola
(74) *Attorney, Agent, or Firm* — Bacon & Thomas, PLLC

(57) ABSTRACT

An ion-selective electrode comprising: a housing, which surrounds a housing interior; an ion-selective membrane; especially a polymer membrane; and a sensing system, which is in contact with the ion-selective membrane, for sensing a potential of the ion-selective membrane, wherein the ion-selective membrane at least partially fills the housing interior, and is in contact with a medium surrounding the housing via at least one traversing bore through a housing wall of the housing.

23 Claims, 6 Drawing Sheets

(56) References Cited

FOREIGN PATENT DOCUMENTS

| | | |
|---|---|---|
| DE | 3725597 A1 | 2/1989 |
| DE | 102006012651 A1 | 9/2007 |
| FR | 2 382 009 | 9/1978 |
| WO | 9004777 A1 | 5/1990 |
| WO | WO 2010/072510 A1 | 7/2010 |

OTHER PUBLICATIONS

Mei Duo, "Studies on Simultaneous Determination of Multicomponent by Ion-Selective Electrodes Analytical Method", Tianjin University, Jan. 2005 (the Chinese document and the English translation).

* cited by examiner

ION-SELECTIVE ELECTRODE

TECHNICAL FIELD

The invention relates to an ion-selective electrode (ISE) including: A housing, which surrounds a housing interior; and an ion-selective membrane, especially an ion-selective polymer membrane, which comprises at least one selectivity-providing component; and a sensing system arranged within the housing for sensing a potential of the polymer membrane.

BACKGROUND DISCUSSION

In general, such electrochemical sensors, in the case of which the relative change in the equilibrium Galvani voltage between a measured medium and a sensing electrode is preferably effected by the activity change of predominantly a certain kind of ion, are referred to as ion-selective electrodes. Such ion-selective electrodes allow relatively simple and fast determining of ion concentrations in different media, e.g. also in turbid and colored solutions. Ion-selective electrodes are applied, for example, in process-liquid analysis or in waste water analysis.

Potentiometric measurements with ion-selective electrodes metrologically correspond largely to classic pH measurements technology on the basis of pH glass membrane electrodes. Referencing a reference potential of a reference electrode with an essentially constant potential, e.g. the known Ag/AgCl electrode, the ion concentration in a measured medium can, by means of a high-impedance voltmeter, be determined with high accuracy with little apparatus-related effort.

Besides glass membranes, so-called solid body or polymer membranes are also currently used as ion-selective components of such electrodes. The latter comprise, as a rule, a so-called plasticizer as a lipophilic solvent, a salt of the kind of ion to be measured with a lipophilic counter ion, and a polymer material as a network former for solidification of the membrane. Especially in the case of cation-selective membranes, an ionophore is frequently also present. FIG. 1 schematically shows the basic construction of such a polymer membrane electrode. Ion selective electrodes of this manner of construction are described, for example, in "Ion-selective Electrodes", J. Koryta and K. Stulik, Cambridge University press, 1983, S. 61, or in "Das Arbeiten mit Ionenselektiven Elektroden (Working with Ion-Selective Electrodes)", K. Cammann, H. Galster, Springer, 1996.

The ion-selective electrode 1 includes a tubular housing 2, which is sealed on one end with a closure cap 3, and on the other end by an ion-selective polymer membrane 5, i.e. a polymer membrane including a selectivity-providing component. In the housing interior 7 surrounded by the housing 1, a sensing system is located, which leads the electrical potential of the membrane off to an electrically conductive contact or connection cable 9. The sensing system comprises an inner electrolyte 11 and a sensing electrode 13, which, for example, can be formed of a silver wire coated with silver chloride. The inner electrolyte 11 usually contains a salt of the ion to be determined, as well as additional chloride ions for stabilizing the electrical potential difference between the inner electrolyte 11 and sensing electrode 13. The polymer membrane 5 usually has a thickness of less than 1 mm and is composed as previously described.

With its membrane bearing end, the ion-selective electrode 1 can be immersed in a measured medium, e.g. in a liquid, in which the ions to be detected are dissolved, in order to determine the concentration of a certain kind of ion in this medium. In the case of the electrode construction shown in FIG. 1, in measurement operation, the polymer membrane 5 has contact with the medium across its entire base.

In the case of use of the ion-selective electrode for continuous measured value registering in liquid analysis, the period of use achievable under real conditions is of great importance. As a rule, the ion-selective components and plasticizer of the polymer membrane have low, but nevertheless noticeable, water solubility. This leads to the washing out or bleeding of the selectivity-providing component or of the plasticizer, and therewith to a change in the composition of the polymer membrane, which, in turn, effects a change in the membrane properties. After a period of use of some months in measurement operation, the ion-selective electrode, or the membrane, must therefore be replaced. The average period of use of an ion-selective polymer membrane electrode is, in addition to the solubility of the membrane components in the measured medium, also influenced by the thickness or the volume of the membrane. Also the flow velocity of the measured medium, and in given cases surfactants or organic solvent present in the measured medium, can increase the solubility of the membrane components in the measured medium. The washing out of membrane components occurs especially intensively in online measurements technology, in the case of which the ion-selective membrane is continually located in a liquid flow.

The consequences of the washing out of membrane components are, among other things,
   drift of the calibration parameters, slope and zero-point;
   change in the Nernst concentration range, i.e. the range in which a linear relationship between the logarithm of the ion concentration to be measured and the measured voltage exists;
   change in the limit of detection;
   change in the selectivity of the electrode;
   change of the isothermal point of intersection;
   lengthening of the response time.

In WO 93/21520 A1, measures are described for lengthening the period of use of a polymer membrane electrode. These include the saturation or over-saturation of the inner electrolyte and, as far as is possible, also of the measured medium, with the components of the membrane tending toward being washed out. Described in an example of an embodiment is the introduction of a conditioning cartridge into the housing interior of the ion-selective electrode. The cartridge contains all important membrane components tending toward being washed out are present, adsorbed on a highly disperse solid phase with a large specific surface. This highly disperse solid phase is in contact with an aqueous electrolyte solution in the housing interior, so that this is practically continually saturated or over-saturated with the membrane components tending toward bleeding out, and a resupplying of these components to the membrane is achieved. Furthermore, a difficultly soluble salt of the ion to be determined should be placed directly in the membrane. Via the named measures, the period of use of the ion-selective electrode in the case of uninterrupted contact with a measured medium should be increased.

A disadvantage of an ion-selective electrode embodied in such a manner is the fact that the measured medium can be saturated or over-saturated with the membrane components tending toward bleeding only in exceptional cases. In WO 93/21520 A1, it is provided that the measured medium be conducted through a cartridge, in which all important membrane components tending toward being washed out are present, adsorbed on a highly disperse solid, phase with large specific surface. Since in the course of a longer time of use, large volumes of measured medium flow through such an apparatus, it must be assumed that the cartridge will be fouled and clogged by solid and dissolved sample components, or lose its usefulness by other means, for example, through microbial growth.

SUMMARY OF THE INVENTION

An object of the invention is, consequently, to provide an ion-selective polymer membrane electrode which overcomes the disadvantages of the state of the art. Especially an ion-selective electrode with an ion-selective membrane which enables a time of use acceptable for online analysis without additional apparatus-related effort should be provided.

This object is achieved by an ion-selective electrode comprising: a housing, which surrounds a housing interior, an ion-selective membrane, especially an ion-selective polymer membrane, and a sensing system, which is in contact with the ion-selective membrane, for sensing a potential of the ion-selective membrane, wherein the ion-selective membrane at least partially fills the housing interior, and is in contact with the environment surrounding the housing via at least one traversing bore through a housing wall of the housing.

For detection of the kind of ion for which the ion-selective electrode is designed, the housing of the ion-selective electrode is immersed at least so far into a measured medium that the ion-selective membrane is in contact with the measured medium via the traversing bore.

Since the ion-selective membrane is arranged within the housing and is in contact via a traversing bore in the housing wall with the environment surrounding the housing, and in measurement operation especially with the measured medium, the washing out of the components present in the membrane which are soluble in the measured medium—especially also of such components which cause or at least influence the selectivity of the membrane—is, without considerable structural effort, clearly reduced in comparison to the ion-selective electrode shown in FIG. 1, in the case of which, in measurement operation, the ion-selective membrane is in contact with the measured medium with a relatively large area, e.g. of the order of magnitude of the housing diameter.

The housing of the ion-selective electrode is composed of an electrically insulating material, e.g. glass or synthetic material, e.g. plastic. Meant here and in the following by the term "bore" is, in addition to an opening manufactured by means of a rotating tool, also a traversing opening produced by any other method known in the state of the art, e.g. laser ablation, etching or erosion, which produces a connection between the housing interior and the medium surrounding the housing. Furthermore meant by "bore" in the sense of this application is also an opening already present due to the material properties of the housing wall, e.g. a pore. As a traversing bore through the housing wall, the bore has an exit into the housing interior of the ion-selective electrode—in the following also referred to as a membrane-side exit—and an exit to the environment surrounding the housing, in the following also referred to as a medium-side exit.

The terminology "potential of the ion-selective membrane" means the potential arising at the interface between the membrane and a medium in contact with the membrane—for example, in measurement operation, i.e. the measured medium. This potential is also called the "membrane potential".

For reducing the washing out of components soluble in the measured medium, especially the selectivity-providing component of the ion-selective membrane, it is especially advantageous if the lengthwise extension and the diameter of the bore cross section and the diameter of the region of the housing interior filled by the membrane, this area adjoining directly on the bore, are matched to one another in such a manner, that, in the case of a diffusion of a substance, especially of a membrane component, through the bore in a volume region adjoining on the medium-side exit of the bore and/or in a volume region adjoining on the membrane-side exit of the bore, forms a spherical-sector-shaped and especially hemispherical diffusion profile.

This has especially the advantage that the concentration profiles which characterize the washing out of membrane components in the membrane in the region of the bore, in comparison to a concentration profile in the case of planar diffusion, as is formed in the example in FIG. 1, extend only over a short distance into the membrane. Furthermore, the material flux relative to the cross sectional area of the bore is relatively high, so that, despite the continuous bleeding of membrane components, the concentrations of these components at the phase boundary decisive for the signal formation between the membrane and the measured solution almost correspond to those concentrations which are present in the interior of the volume phase of the membrane. An analogous situation is also the case for materials or ions which diffuse through the bore into the membrane.

Their concentration decreases very quickly with increasing distance from the bore, wherein the thickness of the diffusion layer here is also small and constant in time.

Via the spherical-sector-shaped diffusion profile on both sides of the bore, both on the membrane side as well as also on the medium side, material transport occurs very intensively in comparison to an ion-selective electrode according to FIG. 1, i.e. the response time is considerably shortened. Since the size of the diffusion zones at a bore with a diffusion profile which is hemispherical on both sides is relatively small, the diffusion gradients in the membrane or in the measured medium very rapidly reach steady state. In this way, a short response time is assured.

For achieving a spherical-sector-shaped diffusion profile, the bore can have a membrane-side exit into the housing interior, on which borders a spherical-sector-shaped volume element, which is completely filled out by the membrane, and which has a radius of not less than 10 times, especially of not less than 100 times, especially of not less than 10,000 times the radius of the bore and a solid angle of between $1\pi$ and $2\pi$ sr (steradian).

In an additional embodiment, the bore has, in a direction perpendicular to the housing wall, a lengthwise extension of 3 to 300 µm, especially of 3 to 200 µm, especially of 10 to 200 µm. With the "lengthwise extension" of the bore is meant the extent of the bore between its membrane side and its medium-side exit.

The bore is preferably filled with the membrane material, so that the interface between the membrane and the adjoining medium—for example, in measurement operation, the measured medium—is located in the region of the medium-side exit of the bore.

In an additional embodiment, the bore has a cylindrical or a conical shape with a diameter of 1 to 300 µm, especially 1 to 100 µm, especially 5 to 50 µm, at its narrowest location.

In an additional embodiment, the membrane is in contact with the medium surrounding the housing via a number of traversing bores through a housing wall of the housing, wherein the lengthwise extension of the bores amounts to between 3 to 300 µm, especially between 3 to 200 µm, especially between 6 to 12 µm.

For producing a plurality of bores in the housing wall, a nuclear track etching method can be used, in the case of which a plurality of randomly distributed bores forms. In this case, bores with a smaller cross section than in the case of an individual bore can also be used. In an embodiment, in the case of which the membrane is in contact with the surrounding medium via a number of traversing bores through the housing wall of the housing, the inner diameter of the bores can, consequently, be between 0.01 and 300 µm, especially between 0.01 and 100 µm, especially between 0.03 and 3 µm. Very thin bores with a diameter of less than 1 µm have, as individual bores, a disadvantageously high electrical resistance, which can lead to an undesirably high noise for the measurement signal. Via not completely preventable, if also small, input bias currents of the high-impedance measuring amplifier used, in the case of very small bores, an undesired polarization of the interface between the membrane and the measured medium can, moreover, occur. In the case of the presence of a plurality of bores "connected in parallel", these disadvantages are prevented.

In an additional embodiment, the sum of the cross sectional areas of all of the bores amounts to no more than 1%, especially no more than 0.01% of the inner cross sectional area of the—frequently cylindrically embodied—housing of the ion-selective electrode. Correspondingly, the inner cross sectional area of the housing of the ion-selective electrode, in which the membrane is accommodated, amounts to more than 100 times, especially more than 10,000 times the sum of the cross sectional area of all bores. In this way, it is assured that, at each bore, an approximately hemispherical diffusion profile can occur, without the individual diffusion profiles overlapping significantly.

The thickness of the ion-selective membrane amounts to at least 10 times, especially at least 100 times the bore diameter, but not, however, less than 0.1 mm and no more than 30 mm, and especially the thickness lies between 1 and 10 mm. In this way, it is assured that the membrane volume is sufficiently large to form a reservoir, from which the membrane components tending toward bleeding out are resupplied to the phase boundary between the membrane and the measured medium.

For example, in the case of a membrane in contact with the measured medium via a bore with an inner diameter of 1 µm, the thickness of the membrane can be between 0.1 and 30 mm, especially between 1 and 10 mm.

In an additional embodiment, the membrane completely fills the housing interior. This embodiment is advantageous for ion-selective electrodes which are applied in the case of increased pressure.

In an additional embodiment, the sensing system comprises a metal wire, especially a silver wire coated with a difficultly soluble, silver salt.

In an additional embodiment, the membrane is composed of less than 50%, and especially less than 20%, of a network forming or gel-forming component, especially a polymer component. In such case, with an ion-selective electrode of high molecular weight PVC as a network former-containing or gel former-containing membrane, it is advantageous when the membrane is composed of less than 33% high molecular weight PVC, especially less than 20% or even less than 10% of high molecular weight PVC, for producing a gel-like consistency for the membrane.

In an additional embodiment, the housing is composed, for example, of glass or a synthetic material. Especially, the housing wall, which has the mentioned bore, is advantageously composed of glass or a synthetic material. Said housing wall can, for example, be composed of a synthetic foil comprising polyester or polycarbonate.

The housing, which surrounds the housing interior of the ion-selective electrode, can be formed from a single part. It can, however, also be assembled from at least a first housing portion and a housing wall, which has said bore and is connected with the first housing portion. The housing wall, which has the mentioned bore, can, for example, be connected with the first housing portion in a manner such that it is sealed to liquid, especially by adhesion, welding or clamping. In the following, the housing wall which has the bore is also referred to as the separating wall. By the connection, which is sealed to liquid, between the first housing portion and the separating wall, it is assured that the ion-selective membrane arranged in the housing is in contact with the measured medium exclusively via the at least one bore in the separating wall, but not, however, via unsealed connecting locations between the housing portion and the separating wall.

The housing wall which has said bore can essentially be embodied as a planar surface or essentially as spherical cap-shaped surface or as a cylindrical surface. For example, the housing can be embodied in the same manner as the housing of a pH glass electrode, i.e. with a housing region embodied as an essentially cylindrical shaft, which, on an end, is provided with a spherical cap-shaped thin glass wall, wherein the bore is located in the region of the spherical cap-shaped thin glass wall.

In an embodiment, the housing wall which has the mentioned bore, is coated on the measured medium side with a hydrophilic, gel-like layer, especially one made from a polyacrylamide-gel, which especially has a thickness of 5 to 200 µm. This layer forms an additional membrane, which represents, on the side of measured medium, an additional to diffusion barrier, especially for disturbing ions, e.g. surfactant ions, which are large in comparison to the ions to be detected. With the help of this additional layer, the bleeding of components of the ion-selective membrane can be lessened further, and the influence of the flow velocity in the case of a flowing measured medium can be further reduced.

The ion-selective electrode according to one of the above described embodiments can be a component of a single-rod, measuring chain, which, in addition to the ion-selective electrode, has a reference electrode. The ion-selective electrode forms, in this case, the measuring half-cell of the single-rod, measuring chain and the reference electrode forms the reference half-cell.

The single-rod, measuring chain can be embodied, for example, in such a manner, that the housing of the ion-selective electrode has a tubular form, especially a rotationally symmetric tubular form, and the reference electrode includes: A housing containing a reference electrolyte, this housing surrounding the housing of the ion-selective electrode and being completely closed off from the housing interior of the ion-selective electrode; as well as a sensing system for sensing the reference potential.

The invention furthermore includes an arrangement comprising a plurality of ion-selective electrodes according to one of the above described embodiments and a reference electrode, wherein the ion-selective electrodes include ion-selective membranes, especially different ion-selective membranes, which especially are selective to different ion types. Such a arrangement enables the simultaneous detection and/or concentration determining of various ion types in a measured medium. Preferably, the ion-selective electrodes and the reference electrode are integrated into a shared housing. This shared housing can especially comprise a first housing portion, which includes receptacles, in which are in each case accommodated the ion-selective membrane and the potential sensing system of an ion-selective electrode, or the reference electrolyte and the potential sensing system of the reference electrode, and a housing wall connected with the first housing portion in a manner sealed to liquid, wherein the housing wall includes traversing bores, via which the ion-selective membrane of each ion-selective electrode or, respectively, the reference electrolyte of the reference electrode is in contact with the surrounding environment of the housing. In this way, in measurement operation, the ion-selective membranes of the ion-selective electrodes and the reference electrolyte of the reference electrode are in contact with the measured medium.

The invention furthermore includes a flow measuring cell having, integrated into the flow measuring cell, an ion-selective electrode according to one of the above described embodiments, wherein the ion-selective electrode is integrated into at least a first housing portion of the flow measuring cell, and wherein the wall, which has said bore or the mentioned bores, is connected with the first housing portion in a manner sealed to liquid and borders a hollow space flowed through in measurement operation by the measured medium. The hollow space is bordered by the wall which has said bore or the mentioned bores and by at least one second housing portion, wherein the second housing portion has a liquid supply and a liquid drain, which open into the hollow space. In given cases, between the second housing portion and the wall which has the mentioned bore, a space holder, especially an annular space holder, can be provided, wherein the hollow space is, in this case, bordered by the wall, an area of the second housing portion and the space holder.

The lessening, by the embodiments of the ion-selective electrode related above, of the wash out rate of the components of the ion-selective membrane tending toward being washed out is associated with additional advantages:

Due to the slowed washing out, the concentrations of the different materials in the ion-selective membrane likewise change considerably more slowly. Therefore, it can be assumed therefrom that the calibration parameters—especially the electrode slope, as an important characteristic variable of the membrane which is dependent on the membrane composition—likewise change only slowly. This means that the electrode slope needs to be calibrated significantly less frequently than in the case of the up-to-now typical ion-selective electrodes. In this way, a calibrating of the electrode slope by the user of the ion-selective electrode can also be completely omitted during the entire time of use. The ion-selective electrode need then only be calibrated by the manufacturer.

Because of the lessened concentration decline of the membrane components tending toward being washed out, certain components can be present in the membrane in significantly smaller concentration than in the case of the up-to-now typical ion-selective membranes. Smaller concentrations of, for example, the ionophore or the salt of the kind of ion to be measured with a lipophilic counter ion expand the concentration measuring range to smaller concentrations of the ion to be detected. The limit of detection of the ion-selective electrode is thus lowered thereby. A smaller concentration of the liquid ion exchanger leads, moreover, in many cases, to the selectivity of the ion-selective electrode being noticeably improved with respect to disturbing ions at small disturbing ion concentrations.

Since the membrane is largely surrounded by the housing and is only in contact with the measured medium via the bore, the membrane can have a considerably smaller mechanical strength in comparison to the previously used membranes. The means that the portion of the network former or gel former—for example, PVC—in the membrane can be kept smaller, and thus a larger variability in the composition of the membrane is possible.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 2:
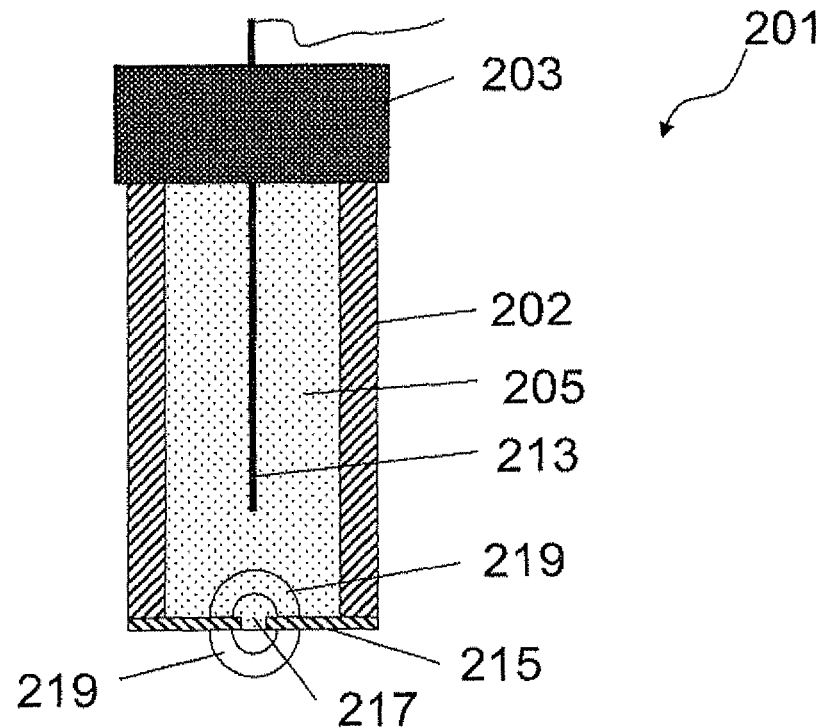
FIG. 2 is a schematic, longitudinal section of an ion-selective electrode, in the case of which the ion-selective membrane is accommodated in the housing interior and is only in contact with a surrounding medium via a traversing bore in the housing wall.

FIG. 2 shows schematically a longitudinal section through an ion-selective electrode 201 having a tubular housing portion 202, which is provided on one end with a closure cap 203 and on the other end with a separating wall 215 connected by means of a liquid tight connection with the tubular housing portion 202. The tubular housing portion 202, the closure cap 203 and the separating wall 215 bound a housing interior, which, in the example shown in FIG. 2, is completely filled with an ion-selective polymer membrane 205. The sensor of the potential arising at the membrane, the so-called membrane potential, is embodied as a solid sensor without inner electrolyte. Serving as a sensing electrode 213 is, in this case, a silver wire coated with silver chloride. The ion-selective membrane 205 is, via a traversing bore 217 in the separating wall 215, in contact with the environment surrounding the ion-selective electrode 201. In measurement operation, the housing portion of the ion-selective electrode 201 provided with the separating wall 215 is immersed in a measured medium, so that the membrane 205 comes in contact with the measured medium in the region of the bore 217.

The bore 217 has preferably a cylindrical or conical shape and a circularly shaped cross section with a diameter of 1 to 300 µm at the narrowest location. The separating wall 215 has a thickness of 3 to 300 µm. As a traversing bore 217 through the separating wall 215, the bore has an exit to the housing interior, also referred to as a membrane-side exit, as well as an exit to the environment surrounding the housing, also referred to as the medium-side exit. At both exits of the bore, there is formed, as shown in FIG. 2, a spherical-sector-shaped—in the case of FIG. 2 a hemispherical—diffusion profile 219 for substances which diffuse out of the environment surrounding the housing into the membrane 205 or out of the membrane into the surrounding environment.

Figure 3A:
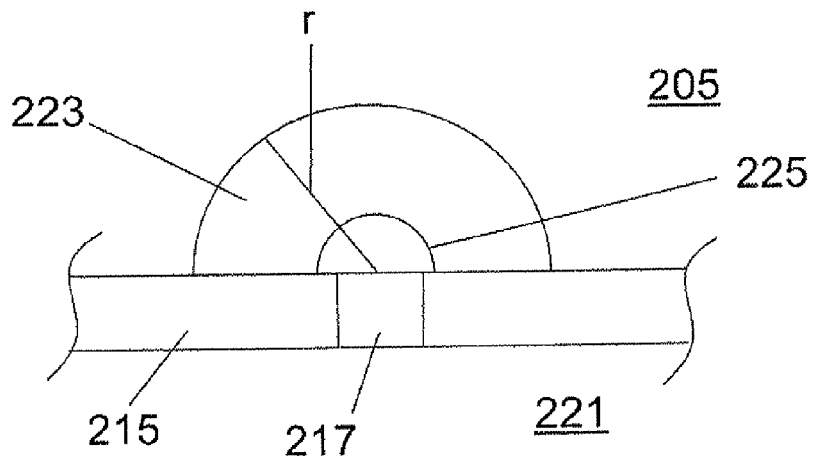
FIG. 3(a) is a representation of a region around the traversing bore in the housing wall of the electrode of FIG. 2.
Figure 3B:
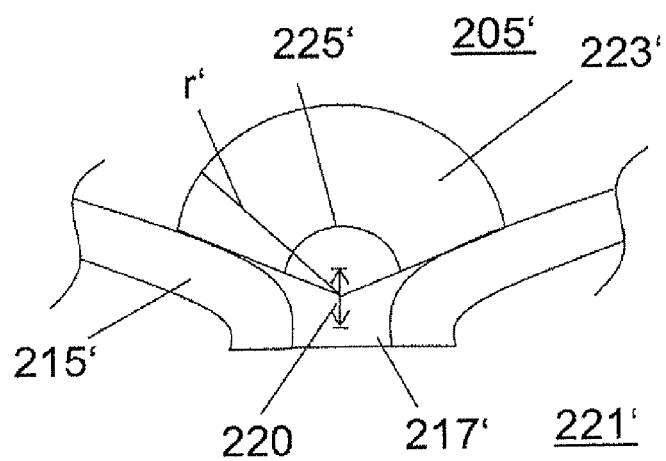
FIG. 3(b) is a representation of an alternative embodiment of the region around the traversing bore in a housing wall of an electrode according to FIG. 2.

FIG. 3 a) shows the sectional illustration of the separating wall 215 enlarged in the region of the bore 217. At the exit of the bore 217 in the housing interior filled with the polymer membrane 205 there adjoins a spherical-sector-shaped—here especially a hemispherical—volume element 223, which is completely filled by the polymer membrane 205. With the term "spherical sector" means a body composed of a spherical segment (spherical cap) and a cone with the circle of the spherical segment as the base and the center of the sphere as the tip. A limiting case is the hemisphere, which here is to be understood as a special case of a spherical sector. The spherical-sector-shaped volume element 223 has a solid angle 325 of $2\pi$ steradian (shown in FIG. 3 a) in sectional illustration) and a radius r, which has a length of not less than 10 times, especially of not less than 100 times or even of not less than 10000 times the radius of the bore 217.

In the example in FIG. 3 a), the exit of the bore 217 occurs abruptly in the form of a step-like transition from the bore 217 to the housing interior filled with the membrane 205, so that the volume element 223 is essentially hemispherical. In FIG. 3 b), a variant is shown, in the case of which the transition from the bore 217' to the housing interior filled with the membrane 205' occurs via a transitional region 220, which, as a rule, extends over a length of no more than twice the diameter of the bore cross section. In this example, the spherical-sector-shaped volume element 223', which adjoins on the exit and is filled completely with the polymer membrane 205', has a solid angle 225' of less than $27\pi$ steradian, since the separating wall 217' is not embodied completely planarly. The radius of the volume element 223' amounts, as in FIG. 3 a), to not less than 10 times, especially not less than 100 times or even not less than 10000 times the radius of the bore 217'.

In the case of such an embodiment of the bore and of the membrane-filled housing interior, there results for diffusion processes from the housing interior to the bore 217, 217' a spherical-sector-shaped diffusion profile. This has the result that the concentration profiles 219, which describe the bleeding of membrane components in the polymer membrane 205, 205' in the region of the bore 217, 217', extend over only a short distance into the membrane 205', i.e. a distance in the order of magnitude of some tens of diameters of the bore cross section. Furthermore, in the case of the presence of a spherical-sector-shaped diffusion profile, the material flux based on the cross sectional area of the bore 217, 217' is so high, that, despite of the continual washing out of membrane components into the measured medium 221, 221', the concentrations of these components at the interface between the polymer membrane 205 and measured medium 221, this interface being decisive for the signal formation of the ion-selective electrode 201, almost correspond to those concentrations which are present in the interior of the membrane. The thickness of the hemispherical diffusion layer, i.e. its extent in the region of the solid angle 225 or 225', is, in the steady state, constant in time and corresponds to about ten to a hundred times the diameter of the bore cross section.

Analogous considerations also hold for the diffusing in of substances which diffuse through the bore 217, 217' into the membrane. Their concentration decreases quickly with increasing distance from the medium-side exit of the bore 217, 217', wherein the dimensions of the spherical-sector-shaped diffusion layer formed in such case lie in the same order of magnitude as for the membrane components diffusing toward the bore 217, 217'.

There forms also in the measured medium in the environment surrounding the bore 217, 217' a spherical-sector-shaped diffusion profile 219 (FIG. 2). This has the result that a fast material transport occurs at the medium-side exit of the bore 217 or 217'. This, in turn, means that the ion-selective electrode 201 responds very rapidly to concentration changes. Furthermore, the low expansion of the spherical-sector-shaped diffusion profile within the measured medium means that, in the case of flowing measured media, the influence of the flow velocity on the measurement signal of the ion-selective electrode is negligible.

In the following, there will now be explained on the basis of a calulational example the advantage of an ion-selective electrode of an embodiment according to FIGS. 2 and 3 as compared to an ion-selective electrode of an embodiment according to FIG. 1 as regards the lessening of the speed of the bleeding membrane components or the shortening of the response time.

Figure 1:
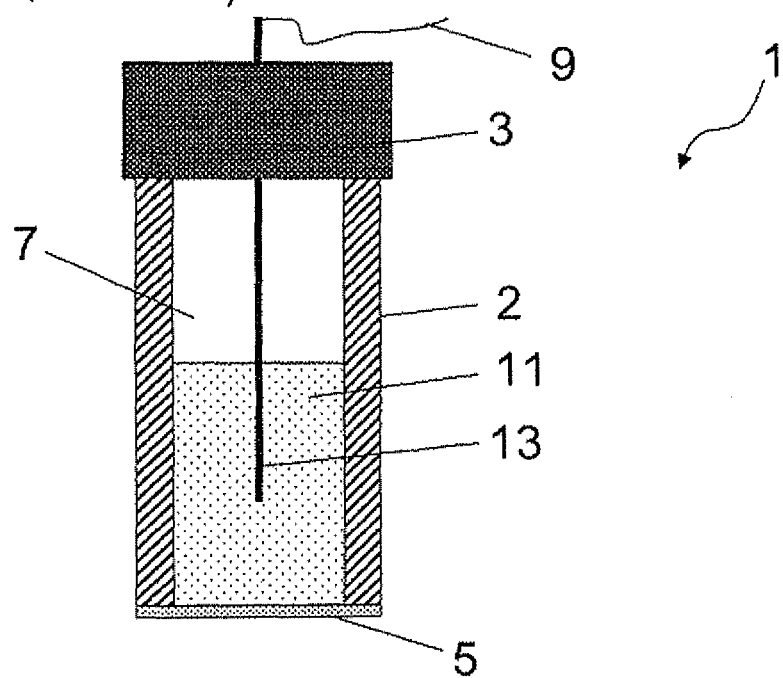
FIG. 1 is a schematic, longitudinal section of a conventional ion-selective electrode.

In the case of a conventional ion-selective electrode according to FIG. 1, a membrane diameter of 12 mm and a thickness of 5 mm are assumed as an example. The membrane surface and the membrane volume are thus 113 mm$^2$ and 565 mm$^3$, to respectively. The speed of the diffusing out of membrane components into a—for example, aqueous—measured medium in the case of a constant temperature approximately follows Fick's Law.

$$\frac{dn}{dt} = \frac{A}{l} D \Delta c, \tag{1}$$

wherein dn/dt refer to the speed of the diffusing out, A to the size of the contact area between the membrane and measured medium, D to the diffusion coefficient of the membrane component diffusing out, l to the average diffusion path and $\Delta c$ to the concentration difference in each case between the center of the membrane and the contact area between the membrane and measured medium, which, for instance, corresponds to half the membrane thickness.

Equation (1) can be reformulated as $$-\frac{1}{D \Delta c} \frac{dn}{dt} = -\frac{A}{l}. \tag{2}$$

The speed the diffusing out normalized by the concentration difference $\Delta c$ and the diffusion coefficients D thus amounts in the case of the described numerical example to 22.6 mm, when a middle diffusion path length of 5 mm is taken as a basis. (The unusual unit of mm for a diffusion rate is to be attributed to the normalization by the diffusion coefficient and the concentration difference.)

For comparison, an ion-selective electrode with a construction according to FIG. 2 or 3 with a membrane of 10 mm diameter and 5 mm thickness will now be considered. The membrane volume correspondingly amounts to 393 mm$^3$. The diameter of the bore is selected to be 20 µm. In the case of a bore of this small cross section, because of the hemispherical diffusion profile, which forms, the ratio A/l is not decisive for the speed of the diffusing out of membrane components, but rather the thickness of the separating wall and the radius r of the bore cross section:

$$\frac{dn}{dt} = -4Dr\Delta c. \quad (3)$$

Equation (3) can be transformed analogously to equation (2):

$$-\frac{1}{D\Delta c}\frac{dn}{dt} = 4r. \quad (4)$$

The normalized diffusing-out rate in the case of a radius of the bore cross section of 10 μm thus amounts, according to equation (4), to 40 μm. Compared to the conventional ion-selective electrode according to FIG. 1, the leaching-out rate thus sinks to, for instance, 0.17% of the original value.

The speed of the concentration decline of the membrane components tending toward bleeding can be still further lessened by taking into consideration the influence of the volume of the membrane. In the case of a greater membrane volume, the membrane contains a greater supply of the bleeding components and thus forms a reservoir, from which these components diffuse toward the interface between the membrane and measured medium. The concentration decline of the membrane components tending toward bleeding in the region of the bore can thus be still further delayed and the duration of operation or service life of the ion-selective electrode therewith still further lengthened, since the membrane has not merely the usual thickness of a few mm—as a rule, even less than the 5 mm set forth in the above example, e.g. 0.2 to 1 mm—but instead a thickness of up to 30 mm, especially 10 mm.

As already set forth above, a further advantage of the embodiment according to FIG. 2 lies in the fact that the membrane 205 arranged in the housing interior can have a lower mechanical strength in comparison to the membrane 5 of the ion-selective electrode illustrated in FIG. 1, which is affixed outside of the housing interior. This means that the portion of the network former or gel former in the membrane can be kept smaller.

As an example, an ion-selective membrane with PVC as a network former is considered. Such membranes are conventionally produced as follows; compare "Das Arbeiten mit Ionenselektiven Elektroden", K. Cammann, H. Galster, Springer, 1996: All membrane components are dissolved via stirring in a volatile solvent, e.g. tetrahydrofuran or cyclohexanone. The solution is then cast in a glass ring, which sits, sealed to liquid, on a glass plate. The ring is covered with a sheet of filter paper and weighted down with a weight, so that the solvent can gradually evaporate within some days. After drying, the membrane raw material is removed from the glass plate. The application of only small portions of network formers—for example, of small polymer contents—in the ion-selective membrane offers the opportunity to omit the solvent, and to manufacture membranes by mixing the components with heat, casting and subsequent cooling. After cooling, the gel-like consistency of the membrane caused by the polymer network then forms. The process of the removing the solvent, which, under certain circumstances, is very time-consuming, is thus absent.

Figure 4:
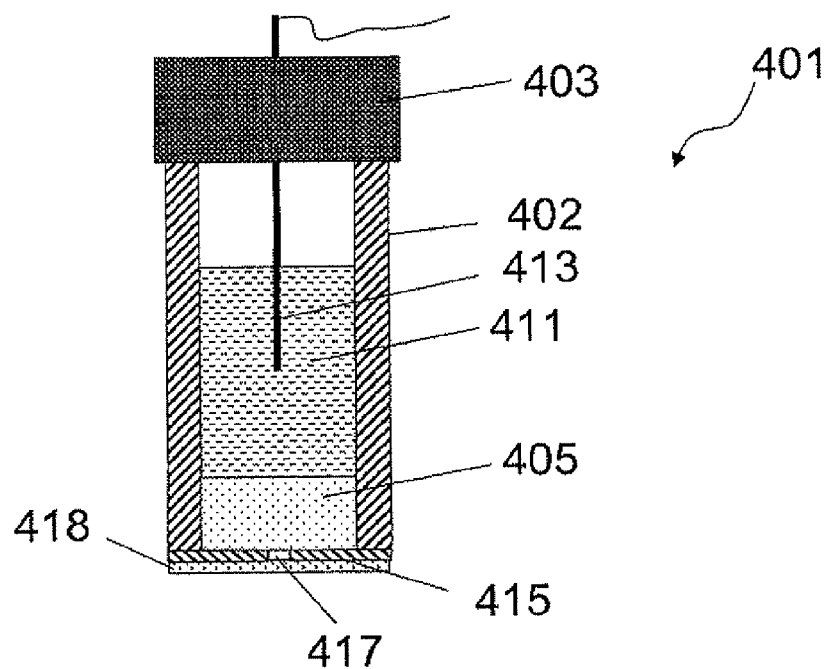
FIG. 4 is a schematic, longitudinal section of an ion-selective electrode according to a first embodiment.

FIG. 4 shows schematically in longitudinal section a further example of an embodiment of an ion-selective electrode. The ion-selective electrode 401 is embodied as a potassium ion-selective (in the following, K$^+$-selective) electrode. Electrode 401 includes a tubular housing portion 402 of 12 cm length and 12 mm outer diameter, on whose one end is connected a closure cap 403 and on whose other end a separating wall 415, embodied as polyester film, via welding with the housing portion 402 in a manner sealed to liquid, in order to form a housing. The polyester film has a thickness of 12 μm, and is centrally provided with a cylindrical traversing bore 417. The bore was produced by means of laser ablation. The region of the housing interior bordering on the separating wall 417 is filled with a K$^+$-selective membrane 405. In the housing interior of the electrode 401, bordering on the membrane 405, is located, serving as sensing system 411, a potassium chloride containing, inner solution, into which, for sensing the electrical potential, a potential sensing electrode 413, for example, a silver wire coated with silver chloride, is submerged. Sensing electrode 413 is led via a feed-through through the closure cap 403 to a high-impedance input of a measuring amplifier or an impedance converter, which outputs the membrane potential as a voltage signal and forwards the amplified or converted voltage signal to a superordinated unit, e.g. a measurement transmitter or a bus coupler, for analog/digital conversion, display and processing. In measurement operation, the electrode 401 is immersed in a measured medium in such a manner, that the K$^+$-selective membrane is in contact with the measured medium via the bore 417.

Optionally, the separating wall 415 can be coated on the medium side with a gel-like hydrophilic layer 418 of 5 to 200 μm thickness. This layer 418 forms an additional membrane, which presents an additional diffusion barrier on the side of the measured medium. With the assistance of this additional layer 418, the bleeding of components of the ion-selective membrane 405 can further lessened and the influence of the flow velocity in the case of a flowing measured medium can further be reduced. Moreover, the layer 418 inhibits possibly disturbing ions with relatively large molecular masses, e.g. surfactants, in their movability more strongly than the smaller ions which are to be detected, in the present example K$^+$-ions. In this way, an improved selectivity relative to large disturbing ions, especially surfactant ions, can be achieved.

The K$^+$-selective membrane 405 is composed, for example, of 65.5% dioctyl sebacate, 33.3% high molecular weight PVC, 1% valinomycin and 0.2% potassium-tetrakis-(4-chlorophenyl)-borate. During manufacture of the ion-selective electrode 401, the named components are dissolved in cyclohexanone, and the solution is brought into the housing interior of the electrode 401. The cyclohexanone is removed from the membrane over a number of days via evaporation, in given cases, with use of a vacuum. After complete evaporation of the cyclohexanone, the inner solution is filled in, and the housing is sealed with the closure cap 403. The optionally provided medium-side layer 418 is composed, for example, of a polyacrylamide-gel, which, after the introduction of the membrane and the closing of the housing, is applied in a precrosslinked state to the separating wall 415 and then is crosslinked in-situ.

Figure 5:
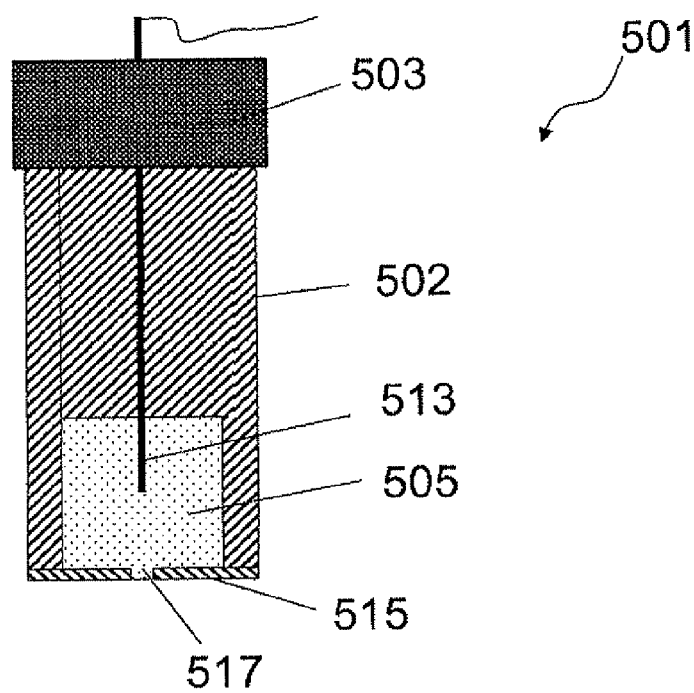
FIG. 5 is a schematic, longitudinal section of an ion-selective electrode according to a second embodiment.

FIG. 5 shows schematically in longitudinal section a further example of an embodiment of a nitrate-selective electrode 501. As in the example in FIG. 4, electrode 501 has a cylindrical housing portion 502 of 12 cm length and 12 mm outer diameter made from an electrically non-conductive material and having on its one end a closure cap 503, and on its opposite end, as a separating wall 515, a polyester film connected via adhesion or via welding with the housing portion 502, so that a housing is formed in which the ion-selective membrane 505 is accommodated. The housing portion 502 is embodied in a region adjoining the closure cap as a solid rod made of the electrically non-conductive housing material and transitions into a region adjoining the separating wall 515 in the form of a tubular housing region. The solid region of the housing portion 502, the polyester film 515 as well as the tubular housing region bordering on the separating wall 515 bound a housing interior completely filled with a nitrate-selective membrane 505. The polyester film has a thickness of 6 μm and is provided in a central region with a traversing, cylindrical bore 517—produced, for example, via laser ablation—with a diameter of 20 μm. If the electrode 501 is immersed with its region which is provided with the separating wall 515 in a measured medium, the nitrate-selective membrane 505 is in contact with the measured medium via the bore 517. Serving as potential sensing system in the present example is a sensing electrode 513 in contact with the nitrate-selective membrane 505. This electrode serves as a solid sensor without an additional inner electrolyte. The sensing electrode 513 is, for example, a silver wire coated with silver-tetrakis-(4-chlorophenyl)-borate. The amplification or conversion and forwarding of the membrane potential occur in a manner analogous to that for the $K^+$-selective electrode illustrated in FIG. 4.

Since the housing interior of the ion-selective electrode 501 is completely filled with the nitrate-selective membrane 505, the nitrate-selective electrode 501 can also be applied in the case of increased pressure, without it being sensitive to pressure fluctuations. When, as a result of temperature fluctuations, the housing and the membrane 502 expand to different degrees, a small deformation of the separating wall 515 of polyester film occurs, whereby a pressing out of membrane material, or a sucking in of sample solution is prevented.

The nitrate-selective membrane 505 is made, for example, from 94.9% 2-Nitrophenyl-n-octyl ether, 5% high molecular weight PVC and 0.1% tridodecylmethylammonium nitrate. The manufacture of the membrane 505 occurs by mixing and stirring the components on a water bath and by casting in the preheated housing of the ion-selective electrode. In such case, as already described earlier, due to the small PVC portion, a solvent can be omitted, which significantly simplifies the manufacture.

Figure 6:
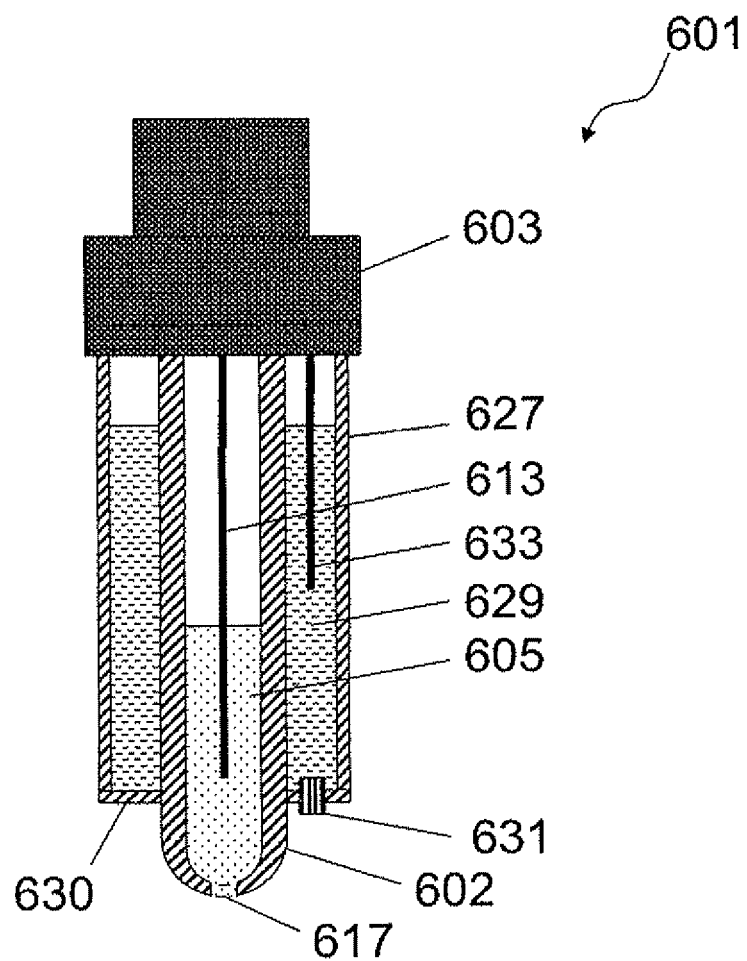
FIG. 6 is a schematic, longitudinal section of a single-rod, measuring chain with an ion-selective electrode according to a third embodiment as a measuring half cell.

FIG. 6 shows a single-rod, measuring chain 601 having a nitrate-selective electrode as measuring half cell. The measuring half cell of the single-rod, measuring chain 601 includes a first tubular housing portion 602 with an inner diameter of 4 mm, made of an electrically non-conductive material—in the example described here, glass. In its first end region, first tubular housing portion 602 connects with a sensor plug head 603, and, in its second end region, it transitions into a thin-walled, spherical cap-shaped, housing wall, which, together with the housing portion 602 and the sensor plug head 603, bounds a first housing interior, the measuring half cell interior. The spherical cap-shaped, housing wall has a wall thickness of, for instance, 200 μm, and is provided with a traversing bore 617, produced, for example, by means of laser ablation. Bore 617 possesses a cross section with a diameter of 20 μm. The section of the measuring half cell interior bordering on the spherical cap-shaped housing wall with the bore 617 is filled with a nitrate-selective membrane 605, into which protrudes a potential sensing electrode 613 serving as a solid sensor without an inner solution and composed, for example, of a silver wire coated with silver chloride. Sensing electrode 613 is connected in an electrically conductive manner with an electronic circuit arranged in the sensor plug head 603.

The nitrate-selective membrane 605 is composed of 94.9% 2-Nitrophenyl-n-octyl ether, 5% high molecular weight PVC and 0.1% tetradodecylammonium nitrate. Membrane 605 can be produced by mixing and stirring the components on a water bath, and installed by casting into the preheated measuring half cell interior, which was, for example, earlier hydrophobized with a silane.

Tubular housing portion 602 is surrounded by an outer shaft tube 627 made of glass or synthetic material, which has an outer diameter of 12 mm. The outer shaft tube 627 is arranged concentrically to the tubular housing portion 602, and on its one end, is connected with the sensor plug head 603, while on its end opposite the sensor plug head 603, it is bordered by an annular frontside housing wall 630, which is connected with the outside of the tubular housing portion 602 in a manner sealed to liquid. The outer shaft tube 627, the tubular housing portion 602, the sensor plug head 603 and the annular frontside housing wall 630 thus enclose an inner space, the reference half cell interior. The reference half cell interior is at least partially filled with a reference electrolyte 629, for example an aqueous potassium chloride solution, in which is submerged an outer, potential sensing electrode 633, for example, a silver electrode coated with silver chloride. The reference half cell interior is connected via a diaphragm 631 with the environment surrounding the single-rod, measuring chain 601, which, in measurement operation, connects the reference electrolyte 629 with the measured medium. A temperature sensor (not shown) can be provided optionally in the single-rod, measuring chain 601.

The outer sensing electrode 633 is conductively connected with the electronic circuit accommodated in the sensor plug head 603. The electronic circuit conditions the potentials delivered by the sensing electrodes 613 and 633 and forwards the conditioned signals. The sensor plug head 603 forms the primary side of a pluggable connector coupling, via which the single-rod, measuring chain is connected with a superordinated unit, for example, a measurement transmitter. The conditioned signals can be transmitted to the superordinated unit, and there further processed and/or output. The pluggable connector coupling can be embodied as a plug contact with a galvanic coupling, or, for minimizing disturbing electrical influences, as a plugged connection with inductive signal and energy transmission.

Figure 7A:
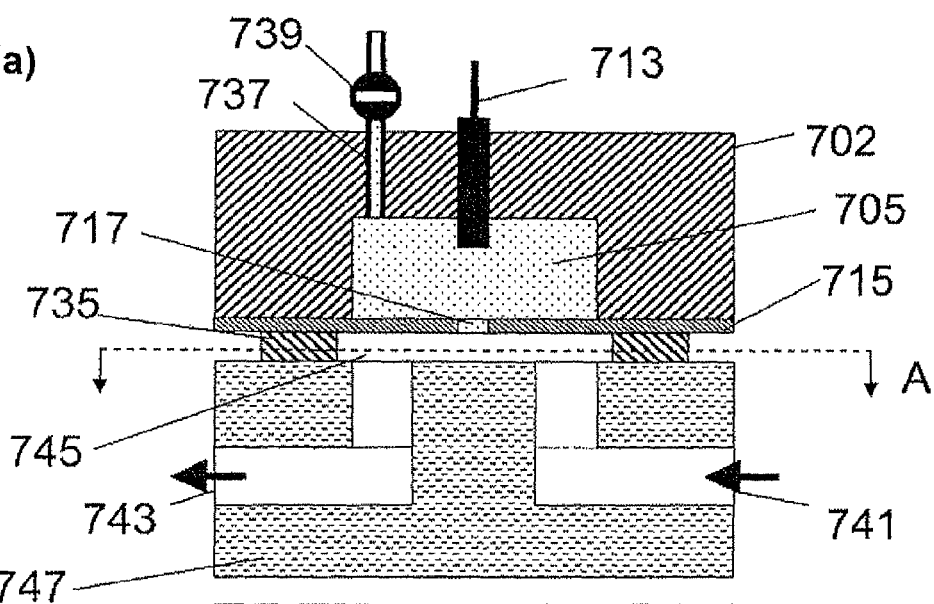
FIG. 7(a) is a schematic, longitudinal section of a flow measuring cell with an ion-selective electrode according to a fourth embodiment.
Figure 7B:
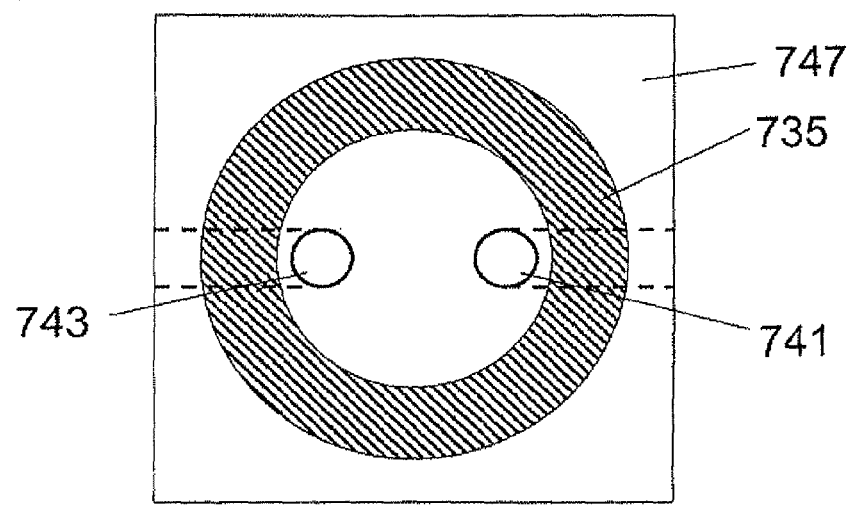
FIG. 7(b) is a schematic, cross section of a flow measuring cell with an ion-selective electrode according to a fourth embodiment.

FIG. 7 shows schematically a flow measuring cell in longitudinal section (FIG. 7 a)) and in cross section taken along the cutting plane A (FIG. 7 b)) for online measurements with an ion-selective electrode. The flow measuring cell can, for example, be used in an analytical system or analyzer, for example according to the embodiment described in the European patent application EP 1 509 774 A1. It can be connected with one or more additional, equally constructed flow through measuring cells with integrated ion-selective or pH value-selective measuring electrodes or with an additional equally constructed flow measuring cell with an integrated reference electrode in such a manner, that, in measurement operation, a measured medium flows through all connected flow through cells, and, in this way, there is formed a measuring chain for measuring pH values and/or ion concentrations referenced to the reference potential of the reference electrode cell.

The flow measuring cell includes a first pot-shaped housing portion 702, which, together with a separating wall 715—which is formed of a polyester film, for example, 12 μm thick, and connected in a manner sealed to liquid with the cylindrical housing portion 702—bounds a housing interior. The housing interior is completely filled by a nitrate-selective membrane 705 of the composition described further above. Via a bore 717 with a cross section of 20 μm in the separating wall 715, the membrane 705 is in contact with a measuring chamber 745, which, in measurement operation, is flowed through by a measured medium. The sensing of potential arising in measurement operation at the interface between the membrane 705 and the measured medium occurs by means of a sensing electrode 713, protruding into the membrane 705, this electrode being led through the first housing portion 702, wherein the amplification and conditioning of the membrane potential occurs as described in connection with FIG. 4.

Due to the fact that the entire housing interior of the pot-shaped housing portion 702 is filled by the membrane 705, the stability of the nitrate-selective electrode is assured even in the case of an excessive or negative pressure in the measuring chamber. Due to the flexibility and elasticity of the polyester film serving as the separating wall 715, the membrane can expand or contract, without the measured medium being pressed out of the measuring chamber into the housing interior, or membrane material being pressed out of the housing interior.

Membrane 705 is produced as described further above in connection with FIGS. 5 and 6 and introduced into the cylindrical cavity in the preheated first housing portion 702. For this, in the example of FIG. 7, a supply line 737 is provided with a valve 739. An example of a material for the first housing portion 702 is polytetrafluoroethylene (Teflon PTFE).

Measuring chamber 745 is bordered by the separating wall 715, a second housing portion 747 and an annular space holder 735. In housing portion 747, a supply line 741 and a discharge 743 are provided for a measured medium, which, in measurement operation, flows through the measuring chamber 745 of the flow measuring cell.

As already indicated above, the flow through cell can be connected with a second, essentially equally constructed flow through cell (not shown) in such a manner, that, in measurement operation, the measured medium flows through the measuring chambers of both flow through cells. The second flow through cell can, instead of the ion-selective membrane 705, include, for example, a reference system—for example, a silver/silver chloride system—which, via a separating wall similar to the separating wall 715, which, for example, has a diaphragm or a bore similar to the bore 717, is in connection with the measuring chamber 745. This second flow through cell, as a reference half-cell, provides a reference potential accessible at a sensor similar to the sensor 713, against which the potential of the ion-selective electrode (as a measuring half cell) connected with it can be measured. With this construction, an ion concentration in the measured medium flowing through can be correspondingly determined. Of course, a number of equally constructed measuring half cells can also be connected with the reference half-cell—for example, arranged cascaded one after the other—in order to in this way simultaneously to determine in the flow the concentrations of various ions, for example, ammonium and nitrate ions, and/or the pH value of the measured medium.

Figure 8A:
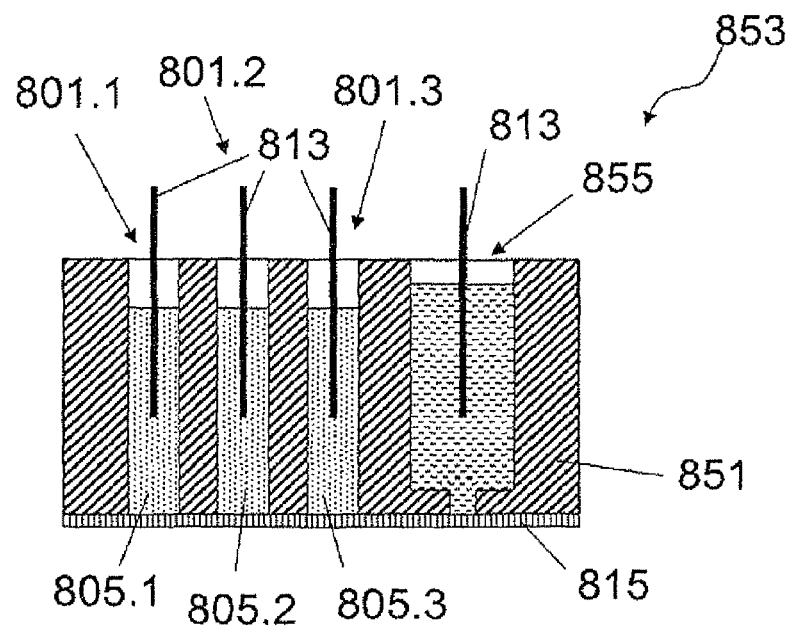
FIG. 8(a) is a schematic, longitudinal section of an arrangement with a plurality of ion-selective electrodes according to a fifth embodiment, and a reference electrode.
Figure 8B:
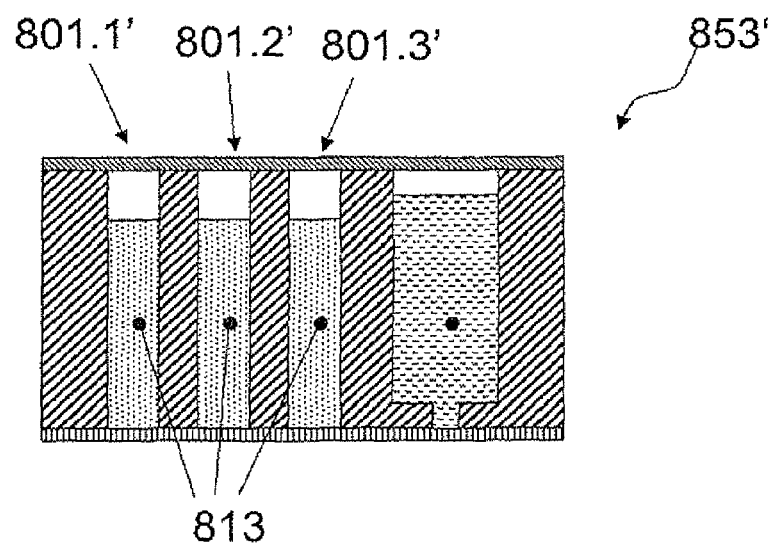
FIG. 8(b) is a schematic, longitudinal section of an alternative embodiment of the arrangement according to a).

FIG. 8 shows schematically a longitudinal section through a arrangement 853 with a plurality of ion-selective electrodes 801.1, 801.2, 801.3 and a reference electrode 855. For better perspicuity, the electrodes are arranged next to one another in this example. Of course, the electrodes can also be arranged in another manner; for example, the ion-selective electrodes 801.1, 801.2, 801.3 can also be arranged around the reference electrode.

The arrangement includes a housing portion 851, into which the ion-selective electrodes 801.1, 801.2, 801.3 as well as the reference electrode 855 are integrated. The housing interior of the ion-selective electrodes 801.1, 801.2, 801.3 and the reference electrode is 855 is, in each case, formed by a cylindrical bore in the housing portion 851. The housing interior of each of the electrodes is bordered on the one end by a closure (not drawn), and on the opposite end—which, in measurement operation, is submerged in the measured medium—by a separating wall 815, for example, a synthetic foil 815, especially one of polyester. In the example of FIG. 8, all of the electrodes are bordered by a plastic foil serving as the separating wall 815, which is shared by all of the electrodes, is connected in a manner sealed to liquid—e.g. via adhesive or welding—with the housing portion 851, and has a plurality of bores. Advantageously, a nuclear track membrane is used for this. Such nuclear track membranes are commercially available. The nuclear track membrane is embodied in such a manner that it contains a plurality of pores produced by nuclear track etching, which are sufficiently small or are arranged sufficiently far apart from one another, that, on the membrane side and on the medium side, as described above in connection with FIGS. 2 and 3, a spherical-sector-shaped—especially a hemispherical—diffusion profile for materials passing through a particular pore forms in each case. For example, a nuclear track membrane with a pore density of $5 \cdot 10^4$ cm$^2$, with an average pore diameter of 0.2 µm can be used. The sum of the pore cross sections amounts in the case of such a nuclear track membrane on an area of 1 cm$^2$ to $0.157 \cdot 10^{-4}$ cm$^2$, which corresponds to an area fraction of 0.0016% with reference to the area of the nuclear track membrane. This ratio of total pore cross sectional area to separating wall or housing cross sectional area is, as previously described, sufficiently small to assure the previously described advantages for the ion-selective electrodes 801.1, 801.2, 801.3.

Each of the ion-selective electrodes 801.1, 801.2, 801.3 includes an ion-selective membrane 805.1, 805.2, 805.3 and a sensing system, which, for example, can be embodied as a solid sensor without an inner solution, as described in connection with FIG. 4. The ion-selective electrodes 801.1, 801.2, 801.3 especially contain different membranes 805.1, 805.2, 805.3, which address different ion types, e.g. ammonium, nitrate, nitrite and potassium. Thus, the arrangement 855 can be applied for monitoring a plurality of ion concentrations, for example in waste water.

The housing interior of the reference electrode 855 contains a reference electrolyte, for example, an aqueous potassium chloride solution. In the case of the reference electrode, the nuclear track membrane forms the diaphragm via which the reference electrolyte is connected electrolytically with the measured medium. The housing interior tapers in the region adjoining on the separating wall 815. In this way, relative to the ion-selective electrodes 801.1, 801.2, 801.3, the reference electrolyte is in connection via a smaller number of holes of the nuclear track membrane. In this way, loss of reference electrolytes into the measured medium can be limited, and the service life of the reference electrode 855, and therewith of the entire arrangement 853, is thus lengthened. Into the reference electrolyte is submerged a sensing electrode for sensing the reference potential.

The sensing electrodes 813 of the sensing systems of the ion-selective electrodes 801.1, 801.2, 801.3, as well as that of the reference electrode 855 are led with separate connection wires to the respective high-impedance input of a measuring amplifier or impedance converter of a measuring electronics, which outputs the voltages of the respective channels and forwards the amplified or conditioned voltage signals to one or more superordinated units for analog/digital conversion, display, and processing.

In a variation of the arrangement 853 according to FIG. 8 b), the sensing electrodes 813' do not extend axially into the cylindrical housing internal spaces as in FIG. 8 a), but instead extend radially or diagonally. In this way, the housing internal spaces of the ion-selective electrodes 801.1', 801.2', 801.3' can be closed with a film 857 at their end opposite the nuclear track membrane 815 in a manner sealed to liquid.

The invention is not limited to the illustrated examples of embodiments and includes every other technically possible type of implementation which falls within the scope of the following claims. Thus, for example, in the case of each of the shown examples of embodiments of ion-selective electrodes, instead of a polyester film with a single bore, a film with a plurality of bores, especially a nuclear track membrane, can be provided. Furthermore, the single-rod, measuring chain according to FIG. 6 can have a different embodiment of the ion-selective electrode serving as the measuring half cell, for example, one according to one of FIGS. 2 to 5.

The invention claimed is:

1. An ion selective electrode, comprising:
  a housing, which surrounds a housing interior;
  an ion-selective membrane; and
  a sensing system which is in contact with said ion-selective membrane, for sensing a potential of said ion-selective membrane, wherein:
  said ion-selective membrane at least partially fills said housing interior and is in contact with a medium surrounding said housing via at least one traversing bore through a housing wall of said housing; and
  the diameter of said bore and the diameter of a region of said housing interior, which region is filled by said membrane and adjoining directly on said bore are matched to one another in such a manner that, in case of diffusion of a substance through said bore, a spherical-sector-shaped diffusion profile forms in a volume region adjoining a membrane-side exit of said bore.

2. The ion selective electrode as claimed in claim 1, wherein:
  the diameter of said bore and the diameter of the region of said housing interior filled by said membrane and adjoining directly on said bore are matched to one another in such a manner that, in case of diffusion of a substance through said bore a hemispherical diffusion profile, forms in a volume region adjoining a medium-side exit of said bore or in said volume region adjoining the membrane-side exit of said bore.

3. The ion selective electrode as claimed in claim 1, wherein the bore has a lengthwise extension of 3 to 300 μm.

4. The ion selective electrode as claimed in claim 1, wherein:
  said bore has a cylindrical or conical shape with a diameter of 1 to 300 μm, at its narrowest location.

5. The ion selective electrode as claimed in claim 1, wherein:
  said membrane completely fills said housing interior.

6. The ion selective electrode as claimed in claim 1, wherein:
  said sensing system includes a metal wire.

7. The ion selective electrode as claimed in claim 6, wherein:
  said metal wire is a silver wire coated with a difficulty soluble, silver salt.

8. The ion selective electrode as claimed in claim 1, wherein:
  said membrane is less than 50% composed of a network forming or gel forming polymer component.

9. The ion selective electrode as claimed in claim 1, wherein:
  said housing wall, which comprises said bore, is connected with the remaining housing in a manner sealed to liquid.

10. The ion selective electrode as claimed in claim 1, wherein:
  the housing wall, which comprises said bore, is embodied essentially as a planar surface or is embodied in an essentially a spherical cap-shaped manner, or as a cylindrical surface.

11. The ion selective electrode as claimed in claim 1, wherein:
  the housing wall, which comprises said bore, is coated on its side facing said medium surrounding the housing with a hydrophilic, gel-like layer, especially one made from a polyacrylamide-gel, which especially has a thickness of 5 to 200 μm.

12. An arrangement comprising:
  a plurality of ion-selective electrodes as claimed in claim 1, and
  a reference electrode, wherein:
  said ion-selective electrodes comprise ion-selective membranes, especially different ion-selective membranes.

13. A flow cell, comprising:
  integrated into the flow cell, an ion-selective electrode as claimed in claim 1, wherein:
  said ion-selective electrode is integrated into at least a first housing portion of the flow cell; and
  the wall, which has said at least one bore, is connected with the first housing portion in a manner sealed to liquid and borders a hollow space flowed through in measurement operation by the measured medium.

14. The flow as claimed in claim 13, wherein:
  the hollow space is bordered by the wall, which has the at least one bore, and by at least one area of a second housing portion; and
  the second housing portion has a liquid supply and a liquid drain, which open into in the hollow space.

15. The flow cell as claimed in claim 13, wherein:
  the hollow space is bounded by the wall, which has the at least one bore, and by at least one area of a second housing portion, as well as a space holder, between the first and the second housing portions; and
  the second housing portion has a liquid supply and a liquid drain, which open into the hollow space.

16. The ion selective electrode as claimed in claim 1, wherein:
  for achieving said spherical-sector-shaped diffusion profile, the ore has a membrane-side exit into the housing interior, on which exit borders a spherical-sector-shaped volume element, which is completely filled by the membrane, and which has a radius of no less than 10 times the radius of the bore and a solid angle of between $1\pi$ and $2\pi$ sr (steradian).

17. The ion selective electrode as claimed in claim 16, wherein the ion selective membrane is an ion-selective polymer membrane.

18. An ion selective electrode comprising:
  a housing, which surrounds a housing interior;
  an ion-selective membrane; and
  a sensing system which is in contact with said anion-selective membrane, for sensing a potential of said ion-selective membrane, wherein:
  said ion-selective membrane at least partially fills said housing interior and is in contact with a medium surrounding said housing via at least one traversing bore through a housing wall of said housing;
  said membrane is in contact with the medium surrounding said housing via a number of traversing bores through a housing wall of said housing; and
  a sum of a cross sectional area of all of the bores amounts to no more than 1%, of an inner cross section of the housing of the ion-selective electrode.

19. The ion selective electrode as claimed in claim 18, wherein:
said inner diameter of the bores amounts to between 0.01 and 300 µm.

20. A sensor arrangement comprising:
an ion-selective electrode comprising;
a housing, which surrounds a housing interior;
an ion-selective membrane; and
a sensing system which is in contact with said ion-selective membrane, for sensing a potential of said ion-selective membrane, wherein:
said ion-selective membrane at least partially fills said housing interior and is in contact with a medium surrounding said housing via at least one traversing bore through a housing wall of said housing; and
a reference electrode; wherein:
the housing of the ion-selective electrode has a tubular form; and
said reference electrode includes: a housing containing a reference electrolyte, surrounding the housing of the ion-selective electrode and being completely closed off from the housing interior of the ion-selective electrode; and
a sensing system for sensing the reference potential.

21. The sensor arrangement as claimed in claim 20, wherein:
said membrane completely fills said housing interior.

22. The sensor arrangement as claimed in claim 20, wherein:
said membrane is less than 50% composed of a network forming or gel forming polymer component.

23. The sensor arrangement as claimed in claim 20, wherein:
said membrane is in contact with the medium surrounding said housing via a number of traversing bores through a housing wall of said housing; and
a sum of a cross sectional area of all of the bores amounts to no more than 1% of an inner cross section of the housing of the ion-selective electrode.

* * * * *